United States Patent [19]

Rasmussen

[11] 3,932,445

[45] Jan. 13, 1976

[54] 2-ARYL-4-(R-METHYL)-5-METHYLIMIDAZOLES

[75] Inventor: Chris Royce Rasmussen, Ambler, Pa.

[73] Assignee: McNeil Laboratories, Incorporated, Ft. Washington, Pa.

[22] Filed: June 26, 1974

[21] Appl. No.: 483,480

[52] U.S. Cl................................ 260/309; 424/273
[51] Int. Cl.$^2$........................................ C07D 233/64
[58] Field of Search.................................... 260/309

[56] References Cited
OTHER PUBLICATIONS

Cornforth et al. Chem. Abst. 1949, Vol. 43, column 2989.

Lawson J. Chem. Soc. (London) 1957, pp. 4225–4228.

*Primary Examiner*—Natalie Trousof

[57] ABSTRACT

2-Aryl-5-methylimidazoles bearing various substituted methyls in the 4-position useful for their ultra-violet (U.V.) absorbing properties.

2 Claims, No Drawings

2-ARYL-4-(R-METHYL)-5-METHYLIMIDAZOLES

DESCRIPTION OF THE INVENTION

The invention relates to novel 2-aryl-5-methylimidazoles having the following formula:

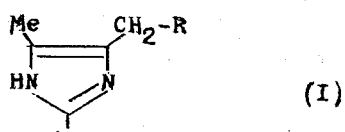

and mineral acid addition salts thereof, wherein Ar is a member selected from the group consisting of phenyl, methylenedioxyphenyl, loweralkanoylphenyl, loweralkylthiophenyl and phenyl substituted with 1 to 3 members selected from the group consisting of loweralkyl, loweralkoxy, halo, hydroxy, phenoxy and nitro; and R is a member selected from the group consisting of COOH, COO(loweralkyl) and CONH$_2$.

As used herein, the prefix "lower" designates a 1 to 8 carbon content for the particular group it modifies; and the term "halo" represents chloro, bromo, fluoro and iodo. Typical mineral acids are the hydrohalic acids and phosphoric sulfuric and the like acids.

The subject compounds may be prepared from the corresponding nitriles of formula (II), wherein Ar is as previously defined, which precursors are described in my copending application Ser. No. 483,251, filed on the same day as the instant application and entitled "2-Aryl-4-Cyanomethyl-5-Methylimidazoles."

The nitriles may be prepared by condensation of an appropriate benzamidine with biacetyl in a suitable loweralkanol to yield 2-Ar-4-loweralkoxymethyl-5-methylimidazole, which is then sequentially converted to the corresponding 4-hydroxymethyl, 4-chloromethyl, and finally the 4-cyanomethyl compound of formula (II) by conventional procedures.

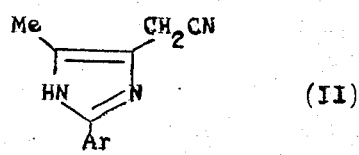

By means of conventional hydrolysis of a nitrile procedures, which may be effected with either acid or base as catalyst, there are obtained upon partial hydrolysis the corresponding amide (III), and upon complete hydrolysis the corresponding carboxylic acid (IV). For example, partial hydrolysis to the intermediate amide may be accomplished by treating the nitrile (II) with concentrated sulfuric acid at room temperature and pouring the resulting solution after completion of amide formation into water. Complete hydrolysis of the nitrile (II) may be effected by refluxing with aqueous or alcoholic alkali or more generally, by refluxing the nitrile (II) with aqueous sulfuric acid (20–70%) or with concentrated (about 40%) hydrochloric or hydrobromic acid. Standard esterification of the acids (IV) with a slight excess of an appropriate lower alkanol affords the corresponding esters (V).

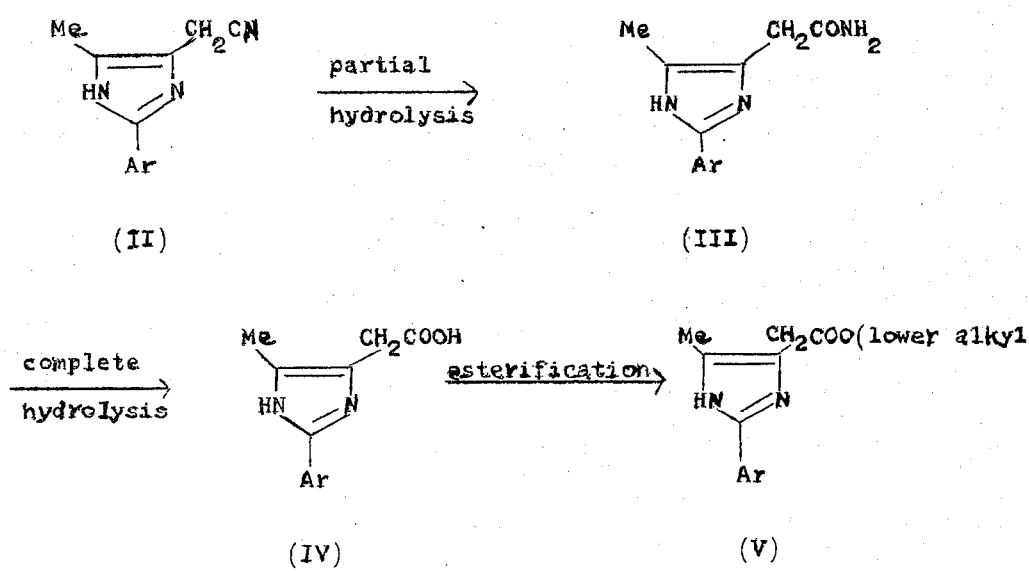

The compounds of formula (I) are obtainable in free base form or in the form of an acid addition salt depending upon the particular isolation conditions employed. The free bases are readily convertible to the salt form by standard treatment with a mineral acid and the salts in turn are readily convertible to the free base form by standard treatment with alkali.

The following compounds of formula (I) are representative of those contemplated by this invention and which may be prepared according to the procedures herein described:

2-p-methylthiophenyl-5-methylimidazole-4-acetamide;
2-p-acetylphenyl-5-methylimidazole-4-acetamide;
2-(2,4-dibromophenyl)-5-methylimidazole-4-acetamide;
2-(2-ethyl-4-isopropoxyphenyl)-5-methylimidazole-4-acetamide;
2-p-n-butoxyphenyl-5-methylimidazole-4-acetamide;
2-p-fluorophenyl-5-methylimidazole-4-acetic acid;
2-(2,4,6-trimethylphenyl)-5-methylimidazole-4-acetic acid;

2-(2,4,6-trichlorophenyl)-5-methylimidazole-4-acetic acid;
2-(4-hydroxy-3-nitrophenyl)-5-methylimidazole-4-acetic acid;
2-p-propionylphenyl-5-methylimidazole-4-acetic acid;
methyl 2-(2-chloro-4-methylphenyl)-5-methylimidazole-4-acetate;
ethyl 2-p-methoxyphenyl-5-methylimidazole-4-acetate;
isopropyl 2-p-n-octylphenyl-5-methylimidazole-4-acetate;
ethyl 2-(3,4-methylenedioxyphenyl)-5-methylimidazole-4-acetate;
butyl 2-m-nitrophenyl-5-methylimidazole-4-acetate; and
ethyl 2-(4-hydroxy-3,5-diiodophenyl)-5-methylimidazole-4-acetate.

The subject compounds (I), in base or acid addition salt form, strongly absorb ultra-violet (U.V.) light, generally above 280 nm, and are useful as U.V.-screening materials, for example, in plastic products and sunburn preventive formulations. Because of their general solubililty in organic materials, the bases may be used as U.V.-absorbers in plastics and resins such as, for example, polystyrene, polyethylene, polypropylene, polyacrylics (e.g., methacrylate resins, polyacrylamides, polyacrylonitrile fibers, etc.), polyamide (e.g., nylon) fibers, and polyester fibers. The inclusion of about 0.01–5.0 percent of the absorber, based on the polymer weight, is usually sufficient to render protection against U.V. light, such as in plastic films, light filters, etc. The absorber may be incorporated into the mixture of monomers before polymerization to form the polymer or it may be incorporated into the polymer at other stages during its handling, as by milling into the polymer together with other compounding ingredients, or during the spinning of the polymer into fibers, etc. The acid addition salts or (I), which are more water-soluble than the base form, are preferably employed as sunscreening agents in typical hydrophylic types of anti-sunburn formulations in amounts of about 0.1–5.0 percent by weight (see G. W. van ham & W. P. Herzog, Chapter 6, "The Design of Sunscreen Preparations," in "Drug Design IV", E. J. Ariens, Ed., Academic Press, N.Y. and London, 1973.

The following examples are intended to illustrate, but not to limit, the scope of the present invention.

EXAMPLE I

5-Methyl-2-phenyl-4-imidazoleacetamide Hydrate:

A mixture of 9.86 (0.05 mole of 5-methyl-2-phenyl-4-imidazoleacetonitrile and 15 ml of concentrated sulfuric acid is stirred and warmed on a steam bath until solution is complete (about 25 minutes). The warm mixture is poured onto excess ice and basified with a slight excess of concentrated aqueous ammonia. Recrystallization from ethanol (95%)-water affords the product, 5-methyl-2-phenyl-4-imidazoleacetamide hydrate, m.p. 186°–188°C. The melting point can be changed to 202°–4°C by thoroughly grinding in an agate mortar. The product can also be made to melt over the range of about 186°–204°C by very slowly raising the oilbath temperature. Treatment with mineral acid, e.g., sulfuric or hydrobromic acid, affords the corresponding acid addition salt.

EXAMPLE II

The partial hydrolysis procedure of Example I may be followed to prepare those compounds of formula (I) wherein R is $CONH_2$. Accordingly, by substituting an equivalent amount of an appropriately substituted nitrile of formula (II) for the 5-methyl-2-phenyl-4-imidazoleacetonitrile used therein, the following respective products are obtained:

2-p-methoxyphenyl-5-methyl-4-imidazoleacetamide;
2-p-chlorophenyl-5-methyl-4-imidazoleacetamide;
2-(3,5-dichlorophenyl)-5-methyl-4-imidazoleacetamide;
2-(3,5-dimethoxyphenyl)-5-methyl-4-imidazoleacetamide;
2-p-n-octylphenyl-5-methyl-4-imidazoleacetamide;
2-(3,4-methylenedioxyphenyl)-5-methyl-4-imidazoleacetamide;
2-p-butylthiophenyl-5-methyl-4-imidazoleacetamide;
2-(4-hydroxy-3-nitrophenyl)-5-methyl-4-imidazoleacetamide;
2-(2,4,6-trimethylphenyl)-5-methyl-4-imidazoleacetamide; and
2-m-nitrophenyl-5-methyl-4-imidazoleacetamide.

EXAMPLE III

5-Methyl-2-phenylimidazole-4-acetic acid Hydrochloride

To 10 ml of concentrated hydrochloric acid (36%) is added 1.36 g (6.9m moles) of 5-methyl-2-phenylimidazole-4-acetonitrile. The homogeneous mixture (hot) is heated on a steam bath for about 3 hours followed by refluxing (mantle) for 1 hour. Cooling and scratching in an ice-bath affords the product, 5-methyl-2-phenylimidazole-4-acetic acid hydrochloride, as colorless crystals. Recrystallization from ethanol-ether or 20% hydrochloric acid gives the pure product, m.p. 228°–230°C (dec.). Treatment with a stoichiometric amount of alkali (e.g., NaOH) affords the corresponding free base form.

EXAMPLE IV

The complete nitrile-to-acid hydrolysis procedure of Example III may be followed to prepare those compounds of formula (I) wherein R is COOH. Accordingly, by substituting an equivalent amount of an appropriately substituted nitrile of formula (II) for the 5-methyl-2-phenylimidazole-4-acetonitrile used therein, the following respective products are obtained:

2-p-butylthiophenyl-5-methylimidazole-4-acetic acid;
2-(4-hydroxy-3,5-diiodophenyl)-5-methylimidazole-4-acetic acid;
2-p-phenoxyphenyl-5-methylimidazole-4-acetic acid;
2-(3-chloro-4-phenoxyphenyl)-5-methylimidazole-4-acetic acid;
2-(4-hydroxy-3-nitrophenyl)-5-methylimidazole-4-acetic acid;
2-m-nitrophenyl-5-methylimidazole-4-acetic acid;
2-(3,4-dimethylphenyl)-5-methylimidazole-4-acetic acid;
2-p-butylphenyl-5-methylimidazole-4-acetic acid;
2-(3,4,5-trimethoxyphenyl)-5-methylimidazole-4-acetic acid;
2-p-acetylphenyl-5-methylimidazole-4-acetic acid; and 2-(3,4-methylenedioxyphenyl)-5-methylimidazole-4-acetic acid.

EXAMPLE V

Each of the acids obtained from Example IV is heated under reflux for a few hours with an excess of anhydrous methanol in the presence of a trace of dry hydrogen chloride to yield the corresponding methyl esters.

EXAMPLE VI

Ethyl 5-methyl-2-phenylimidazole-4-acetate

About 40 g of 5-methyl-2-phenylimidazole-4-acetic acid, 100 ml of absolute ethanol, 1 g of p-toluenesulfonic acid and 650 ml of benzene is heated under reflux with azeotropic removal of water overnight (about 15 hours). The reaction mixture is filtered, washed with sodium bicarbonate solution, dried over anhydrous magnesium sulfate and the solvent evaporated in vacuo to yield the product, ethyl 5-methyl-2-phenylimidazole-4-acetate.

EXAMPLE VII

The procedure of Example VI is repeated except that equivalent amounts of isopropanol and n-butanol are used in place of the ethanol used therein to yield, as respective products, the corresponding isopropyl and n-butyl 5-methyl-2-phenylimidazole-4-acetates.

What is claimed is:

1. A compound selected from the group consisting of 2-aryl-5-methylimidazole-4-acetamide having the formula:

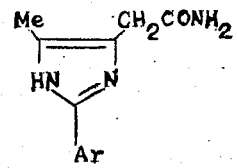

and mineral acid addition salts thereof, wherein Ar is a member selected from the group consisting of phenyl, methylenedioxyphenyl, loweralkanoylphenyl, loweralkylthiophenyl and phenyl substituted with 1 to 3 members selected from the group consisting of loweralkyl, loweralkoxy, halo, hydroxy, phenoxy and nitro.

2. 5-Methyl-2-phenylimidazole-4-acetamide.

* * * * *